United States Patent
Mehl, Sr. et al.

[11] Patent Number: 6,090,085
[45] Date of Patent: Jul. 18, 2000

[54] SKIN MOISTURIZING AND BUFFING DEVICE

[76] Inventors: Thomas L. Mehl, Sr., Tarrion Ct. #3, Apt. 402, Condato, Puerto Rico 00907; Anton H. Clemens, 5854 Schumann Dr., Madison, Wis. 53711

[21] Appl. No.: 08/815,182

[22] Filed: Mar. 11, 1997

Related U.S. Application Data

[63] Continuation-in-part of application No. 08/423,939, Apr. 19, 1995, abandoned, and a continuation-in-part of application No. 08/282,231, Jul. 29, 1994, and a continuation-in-part of application No. 08/066,261, May 25, 1993, abandoned, and a continuation-in-part of application No. 07/929,750, Aug. 17, 1992, abandoned, which is a continuation-in-part of application No. 07/707,028, May 30, 1991, abandoned.

[51] Int. Cl.[7] ..................................................... A61F 7/00
[52] U.S. Cl. .......................................... 604/291; 604/289
[58] Field of Search ..................... 604/113, 114, 604/289, 290, 291; 219/221, 222, 227, 229, 401

[56] References Cited

U.S. PATENT DOCUMENTS

| | | |
|---|---|---|
| 1,552,455 | 9/1925 | Shaler . |
| 1,693,248 | 11/1928 | Newton . |
| 1,772,501 | 8/1930 | Shelton . |
| 1,835,613 | 12/1931 | Perlman . |
| 1,889,487 | 11/1932 | Nachies . |
| 2,021,389 | 11/1935 | Seedorff . |
| 2,187,076 | 1/1940 | Erickson . |
| 2,267,547 | 12/1941 | Zimmerman . |
| 2,285,105 | 6/1942 | Laszlo . |
| 2,437,402 | 3/1948 | Palmer, Jr. . |
| 2,736,317 | 2/1956 | Alexander . |
| 2,739,586 | 3/1956 | Preis . |
| 2,787,998 | 4/1957 | Grossi et al. . |
| 2,809,630 | 10/1957 | Volker . |
| 3,032,803 | 5/1962 | Walshauser .............................. 604/291 |
| 3,104,662 | 9/1963 | Morawetz . |
| 3,370,583 | 2/1968 | Teranishi . |
| 3,745,306 | 7/1973 | Naritomi . |
| 3,749,092 | 7/1973 | Williams . |
| 3,800,810 | 4/1974 | Mercer . |
| 3,809,977 | 5/1974 | Balamuth et al. . |
| 3,872,336 | 3/1975 | Lin et al. . |
| 3,947,659 | 3/1976 | Ono ......................................... 219/362 |
| 3,994,290 | 11/1976 | Springer et al. . |
| 4,114,022 | 9/1978 | Braulke, III ............................ 219/362 |
| 4,166,473 | 9/1979 | Bauer et al. . |
| 4,292,971 | 10/1981 | Smit et al. . |
| 4,300,556 | 11/1981 | Ochi et al. .............................. 604/291 |
| 4,378,804 | 4/1983 | Cortese, Jr. . |
| 4,399,349 | 8/1983 | Deming et al. . |
| 4,419,302 | 12/1983 | Nishino et al. . |
| 4,526,163 | 7/1985 | Fedders . |
| 4,587,959 | 5/1986 | Ruderian . |

(List continued on next page.)

FOREIGN PATENT DOCUMENTS

| | | |
|---|---|---|
| 404928 | 5/1942 | Canada . |
| 2372606 | 8/1978 | France . |
| 1566486 | 10/1970 | Germany . |
| 54-115949 | 9/1979 | Japan . |
| 4-82587 | 3/1992 | Japan . |
| WO 86/04809 | 8/1986 | WIPO . |

*Primary Examiner*—Ronald Stright
*Assistant Examiner*—David J. Cho
*Attorney, Agent, or Firm*—Shlesinger, Arkwright & Garvey LLP

[57] ABSTRACT

A compact hand-held skin treatment device has a porous, slowly movable surface mounted on its housing that applies steam vapor condensate to the skin, thereby providing a light cleansing buffing action. Steam vapor is generated within a narrow vertical boiling chamber by a small compact electric heating assembly within the housing and located close to the movable porous surface. It provides a sufficient amount of vapor to coat the rotating surface with a layer of condensate to be applied to the skin. The housing also contains a small liquid reservoir, a battery operated power supply and a small motor to provide a self-contained readily operated device.

29 Claims, 6 Drawing Sheets

U.S. PATENT DOCUMENTS

| | | |
|---|---|---|
| 4,596,565 | 6/1986 | Ruderian . |
| 4,597,757 | 7/1986 | Ruderian . |
| 4,616,122 | 10/1986 | Burian et al. . |
| 4,621,641 | 11/1986 | Frank et al. . |
| 4,657,531 | 4/1987 | Choi . |
| 4,676,237 | 6/1987 | Wood et al. . |
| 4,722,326 | 2/1988 | Ruderian . |
| 4,733,655 | 3/1988 | Smal . |
| 4,745,909 | 5/1988 | Pelton et al. . |
| 4,868,984 | 9/1989 | Elsherbini . |
| 4,918,818 | 4/1990 | Hsieh . |
| 4,936,027 | 6/1990 | Tsuji . |
| 5,010,905 | 4/1991 | Snyder et al. . |
| 5,013,241 | 5/1991 | von Gutfeld . |
| 5,098,414 | 3/1992 | Walker . |
| 5,103,809 | 4/1992 | DeLuca et al. . |
| 5,121,541 | 6/1992 | Patrakis . |
| 5,241,974 | 9/1993 | Tsai . |

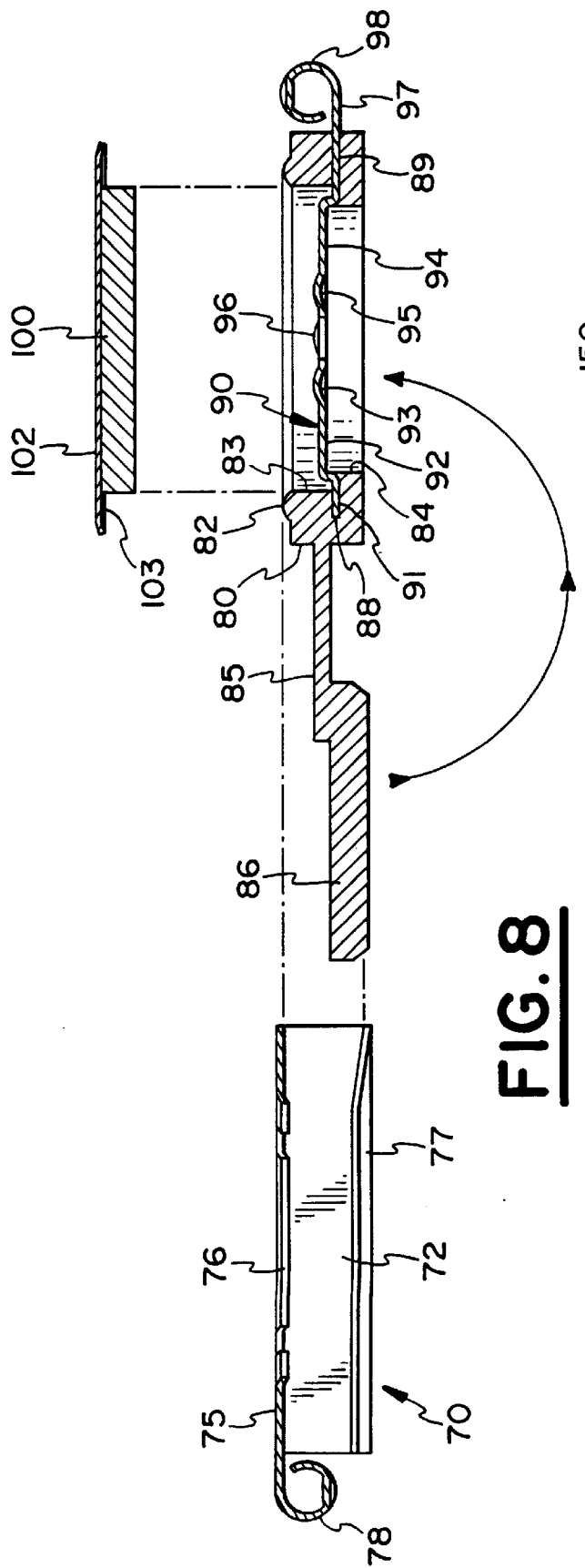
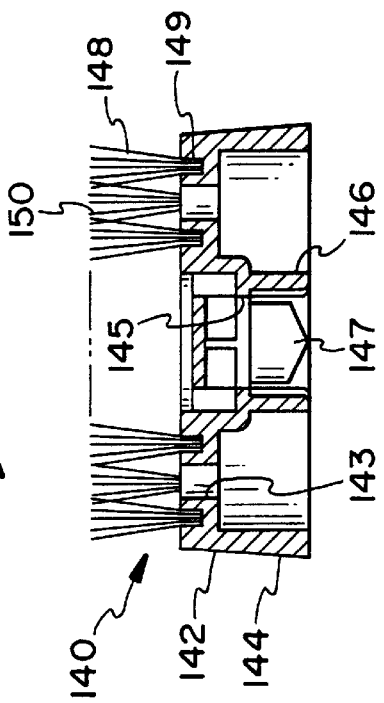
FIG. 8
FIG. 9

SKIN MOISTURIZING AND BUFFING DEVICE

This application is a continuation-in-part of application Ser. No. 08/423,939, filed Apr. 19, 1995, now abandoned; it is also a continuation-in-part of co-pending application Ser. No. 08/282,231, filed Jul. 29, 1994, currently pending; and is a continuation-in-part of Ser. No. 08/066,261, filed May 25, 1993, abandoned; and a continuation-in-part of Ser. No. 07/929,750, filed Aug. 17, 1992, now abandoned; and which was a continuation-in-part of Ser. No. 07/707,028, filed May 30, 1991 abandoned.

FIELD OF THE INVENTION

This invention relates to a skin treatment device, and particularly, to a self-contained, hand-held, consumer usable skin moisturizing and buffing device.

BACKGROUND OF THE INVENTION

There has been a need for an easily usable compact hand-held consumer device for cleansing and moisturizing skin surfaces by a gentle buffing action with warm condensate to open skin pores and reinvigorate skin tissues. This invention is directed to providing such a device. No such device was previously known or available to accomplish this purpose.

FEATURES AND SUMMARY OF THE INVENTION

The user operated moisturizing and buffing device of this invention is a small, compact unit, which is held in the hand of the user, and has a large circular area and movable skin contacting surface. It is primarily designed for use on facial skin surfaces.

The skin contacting surface is mechanically powered to provide a light buff action on the skin surface. In addition to providing a light skin buff action, the contacting surface applies a layer of warm condensed moisture, usually containing water soluble skin treatment substances, to assist in the cleansing and in the moisturizing of the skin tissue it contacts.

The housing of the unit contains a small, fast-heating, high capacity vapor generating system, including a liquid reservoir, a moisture conveying assembly supplying to the skin and a compact steam and vapor heating assembly for contacting surface sufficient moisture in the form of warm condensate to provide for cleansing and moisturizing of the skin surface by the device.

A high rate of vapor generation and an internal fan ensure a sufficient moisture supply for the skin contacting surface. The skin contacting surface is either a thin, porous fiber element or a brush that the vapor passes through and condense upon. The movement of the skin contacting surface provides both a gentle buff contact with the skin, and a continuous supply of moisture for cleansing and moisturizing of the contacted skin tissue.

The moisture conveying and heating components of the vapor generating assembly are mounted on a common support cap to assure rapid assembly and close dimensional tolerances. The heating assembly components of the vapor generating assembly are sealed from vapor exposure to ensure trouble-free operation by precluding corrosion and galvanic deterioration.

This assembly therefore provides a skin rejuvenation device that can be used by the individual in a convenient manner. The application of a warm layer of moisture to the skin to open pores, coupled with a gentle buff action provides a cleansing and moisturizing action not previously possible.

A small closed container of ordinary water, mixed with skin treatment substances usually provides a convenient and effective method of supplying such substances with the device.

A buffing, warm, moist skin surface treatment, and the compact high capacity steam vapor producing assembly are two unique and distinctive features that make possible a skin treatment device that results in a moist and revitalized skin surface. The skin has a pleasing feeling of freshness and smoothness after treatment, which is distinctly noticeable.

In the course of development and testing, it was found that it was necessary to hold the dimensions of the vapor generating assembly to very close tolerances, and to also prevent corrosion in order to obtain good operational capability and long operational life. The small dimensions and close tolerances required for reliable operation dictate that the components are precision made and are readily and very accurately interfitted with each other. This was not initially apparent with prototype models, but was subsequently found to be an important consideration for making a unit having good operational capability and long service life.

BRIEF DESCRIPTION OF THE DRAWINGS

FIG. 8 is a cross-sectional exploded view of the heating assembly of FIG. 6.

FIG. 9 is a cross-sectional view of a rotatable brush unit which can be attached to the housing in place of the rotatable frame of FIG. 2.

DETAILED DESCRIPTION OF THE DRAWINGS

Figure 1:
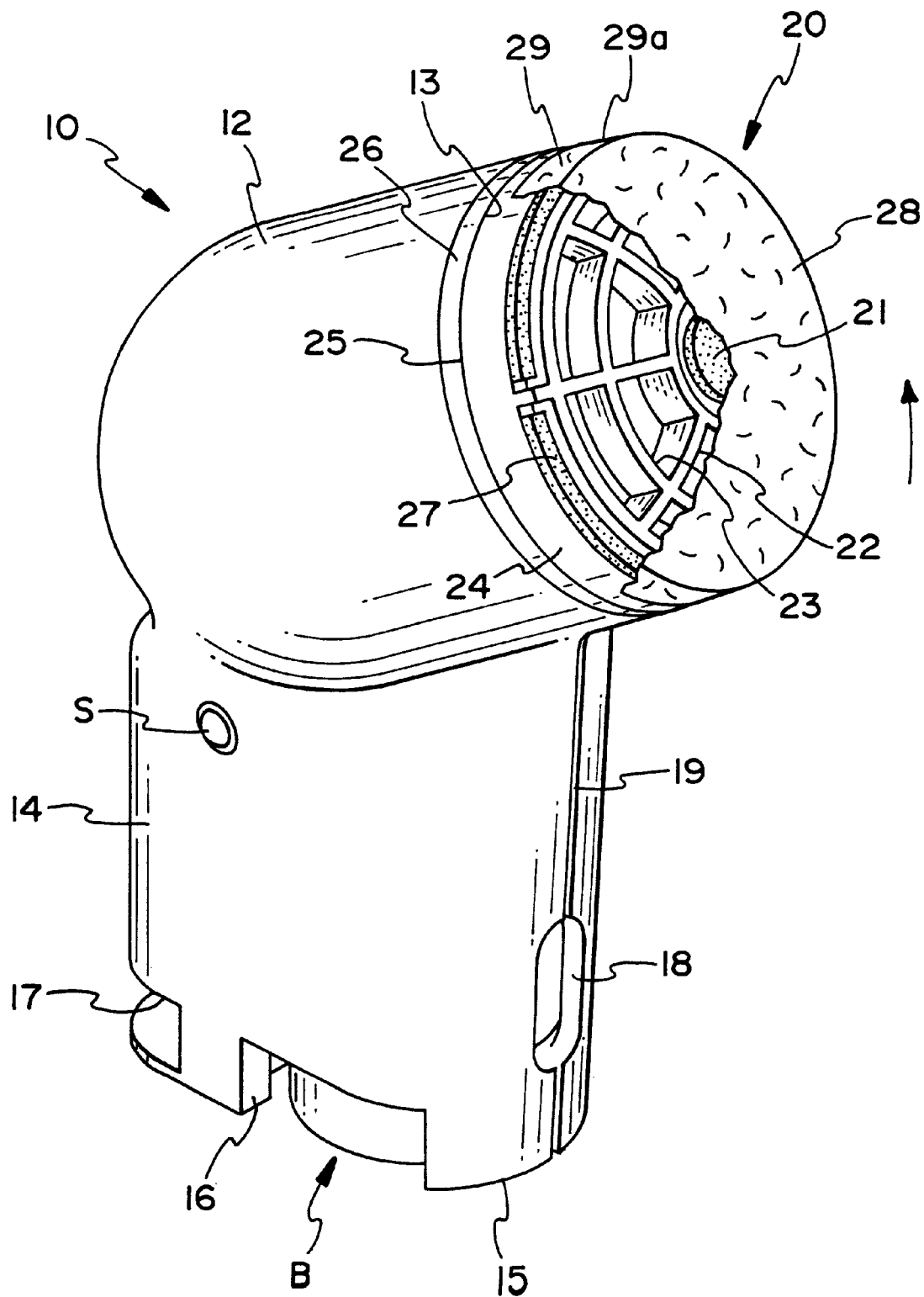
FIG. 1 is a perspective view of the skin moisturizing and buffing device of the invention.
Figure 2:
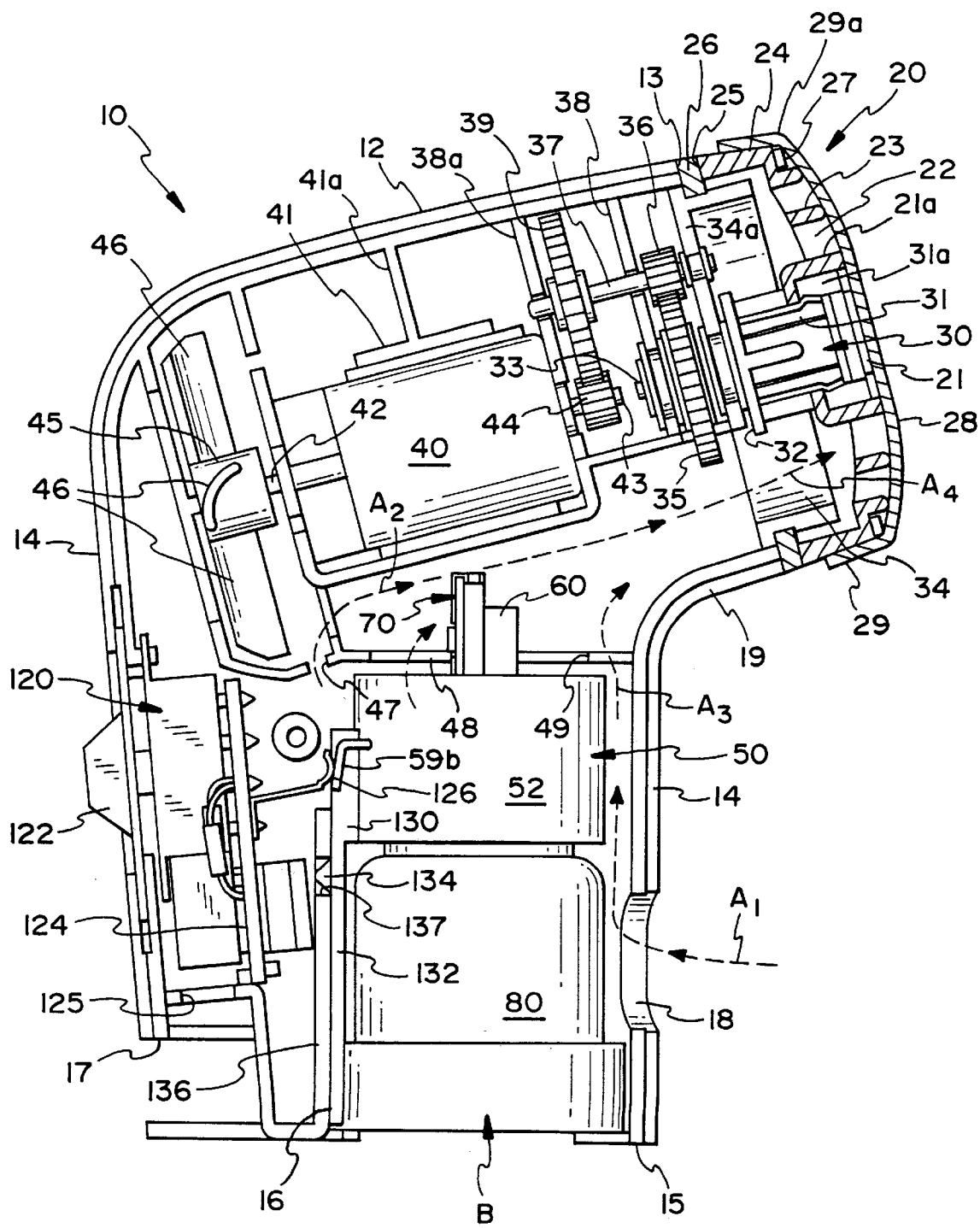
FIG. 2 is a cross-sectional view of FIG. 1.

Referring particularly to the drawings, FIGS. 1 and 2 show the hand-held housing 10 of the moisturizing and buffing device of the invention. The housing is a hand-held pistol grip type, having an upper vapor producing and skin buffing housing section 12, and a lower hand gripped electrical and reservoir housing section 14 slightly over 3 inches long. The lower housing section is open along its bottom forward edge 15, and has an internal cavity into which a liquid supply container B is inserted. The housing is cut out at both bottom sides, as shown at 16, to permit access to the bottom of the liquid container B (reservoir).

The cutout section 17 at the rear end of the housing is open to permit an electrical jack to be inserted up into the electrical power switch assembly of the unit from the bottom.

An air opening 18, at the front of the housing, provides an air intake port for the unit. The housing is a two-piece symmetrical construction joined along line 19 and held together by a transverse extending retaining screw S. It is 2 inches wide and 4 inches high.

A movable skin contacting assembly generally indicated at 20 has an open movable support frame 22 with circular cross grids 23 mounted externally at the open forward end of the upper housing 12. It has a central buff pad retaining button 21 with an external attaching surface, which may be part of a hook-and-loop fastener, such as a VELCRO® brand (DuPont) fastener. An annular flange member 24 has a flat circular bearing surface 25 which engages the annular retaining ring washer 26 mounted on the annular surface 13 of upper housing 12. The outer surface of the annular flange 24 is indented to receive an annular retaining ring 27, which may be a VELCRO® hook and/or loop fastener. The rotating open frame is held in position by the inwardly projecting annular hub section 21a, which has a circular retaining opening.

A porous, filament buffing pad 28 has a pan-shaped configuration, and fits on and over the open frame member and engages retaining button 21. Its annular side 29 fits over the circular section 24 of the open frame and engages retaining band 27.

The buffing pad 28 is circular and has the relatively large diameter of 2 inches. It is approximately one sixteenth inch thick, and is sufficiently porous to permit steam and water vapors to pass there-through and to condense on its surface. The pad texture is soft to the touch when moistened with the water vapor condensed on it. Pressed or woven type fiber pads which have a porosity sufficient to pass vapor through them are usable. Sufficient roughness is required to provide a light buffing action on the surface of the skin during operation. The buffing pad can be a commercially available buff pad used for skin cleansing purposes. A typical commercial pad usable for such purposes is the STRIDEX™ and BUFF PUFF™ and ENVIGORATER™ brand buffing pads. The pads will give a gentle moist exfoliating action. Given such buffing pads, buff pad retaining button 21 and retaining band 27 will typically be the hook portion of a conventional hook-and-loop fastener. Thus, the buffing pad itself detachably attaches as the loop portion of such a fastener. Therefore, the buffing pads can easily be installed or removed.

The power transmitting assembly generally indicated at 30 has a central rotatable prong assembly 31, the fingers of which are resilient, and yielding. They have an external shoulder which passes through and behind the opening of the retaining section 21a to hold the open frame in a mounted position, as illustrated in FIG. 2. The fingers are mounted on a small rotatable circular platform piece 32 which is rotatably mounted on the annular support frame 34. It is positioned in the open front end of the housing 12 immediately behind the retaining ring-bearing washer 26.

Circular platform piece 32 is the output of the speed reduction gear assembly. It is connected to the small drive shaft 33 by a rotatably supported hub mounted on member 34a of support frame 34. Second stage large speed reduction gear 35 is integrally connected to a second rotatable hub mounted on support from 38 to provide reduced speed rotation for the shaft 33. Large gear 35 engages the small gear 36 mounted on shaft 37. Shaft 37 is rotatably supported by the support member 34 at one end, and by inwardly extending motor shaft support member 38a at the other end. The large speed reduction gear 39 of first stage gear reduction is mounted on the inner end of shaft 37 and provides mechanical power from the motor, generally indicated at 40, through spur gear 44 mounted on motor shaft front outer end 43. The motor 40 is held in position by open circular support member 41 and support strut 41a.

The motor shaft rear end 42 is connected to fan hub 45. The fan blades 46 propel air and steam water vapor toward the open front end of the housing and the movable skin contacting assembly 20. The motor shaft rear end 42, and also fan Hub 45, rotates at the operating speed of the motor, as does the front end of the shaft and spur gear 43. The speed reduction gear assembly at the front end of the motor steps down the motor output speed so that, at shaft 33 it is approximately one sixteenth of the motor speed, after passing through the two stage speed reduction gear train 44, 39, 36, and 35. For a typical small 12-volt DC motor having a speed of 8,000 rpm, the speed of gear 33, and therefore, the rotatable pad assembly would be approximately 500 rpm.

Figure 3:
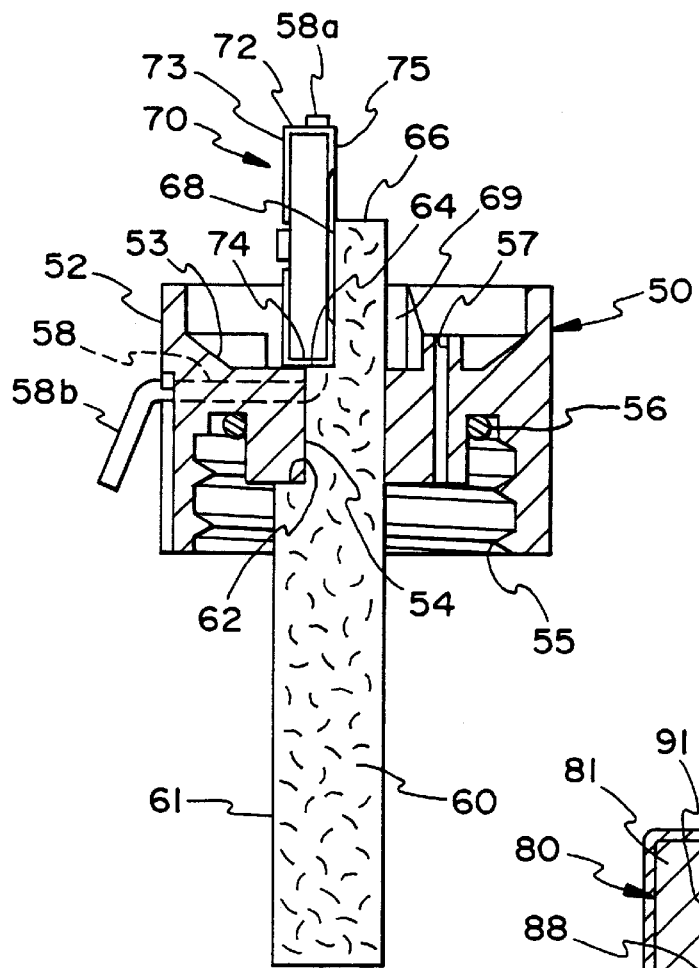
FIG. 3 is an enlarged cross-section of the support arrangement for the moisture supply and steam vapor heating assemblies of the invention.
Figure 4:
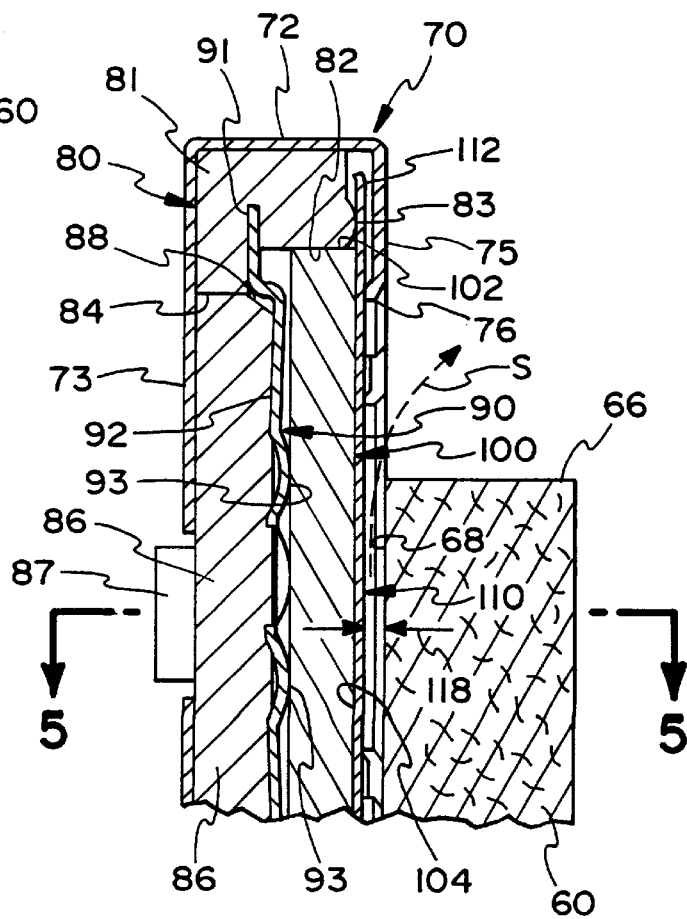
FIG. 4 is an enlarged sectional view of part of FIG. 3 showing, in further detail, the steam vapor heating assembly and the steam vapor generation area.
Figure 5:
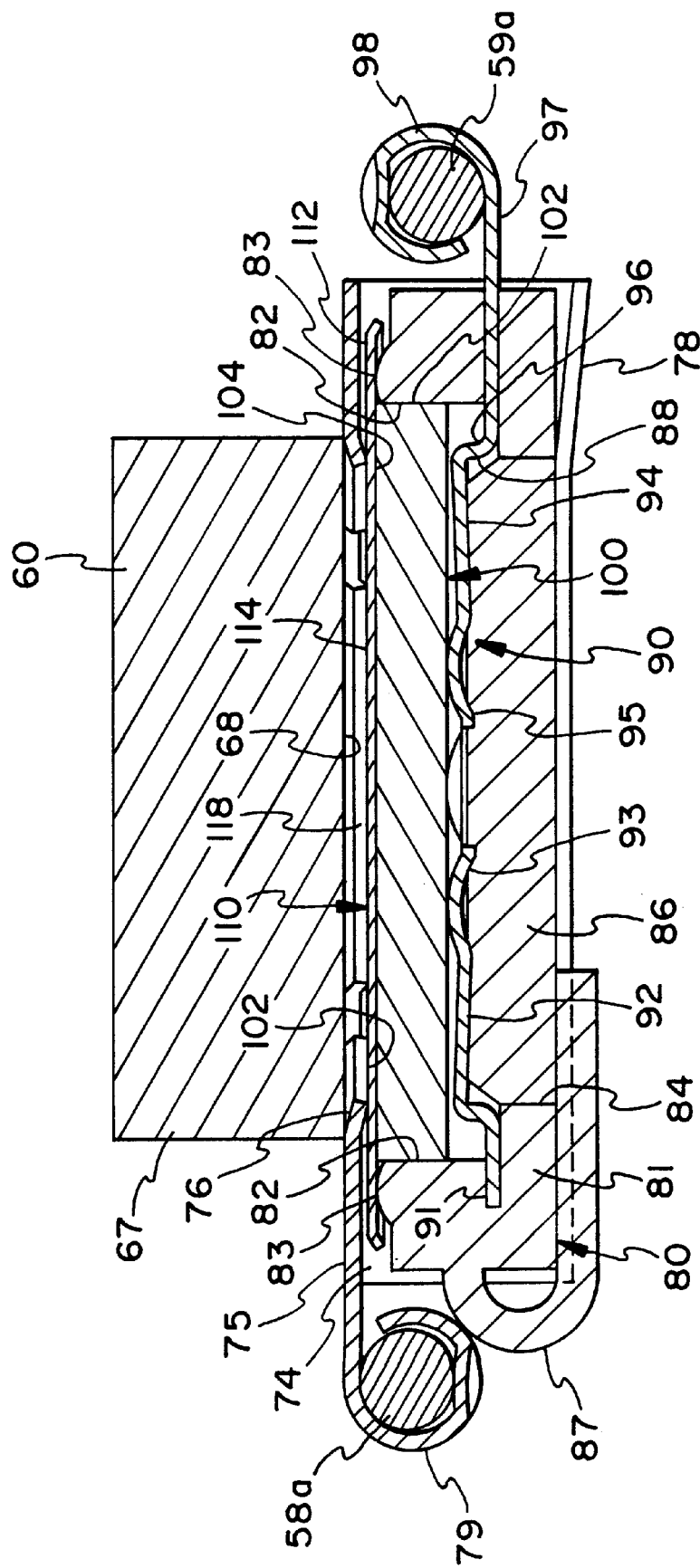
FIG. 5 is a sectional view along line 5—5 of FIG. 4.

Referring to FIGS. 2, 3 and 4 and cross-sectional FIG. 5, the support assembly 50 for moisture carrying and heating elements is provided by the cap 52 for the liquid reservoir bottle 80 (removable bottle B). The bottle is the container for the liquid to be vaporized. The liquid can be ordinary water or water mixed with a water soluble skin treatment substance. The cap 52 has a rectangular opening 54 through the top thereof for receiving a rectangular cross-section wick 60, and internal threads 55 for engaging the threaded neck at the top of the liquid removable and refillable reservoir bottle 80, which it supports. The cap 52 also has a sealing gasket 56, and a vent passageway 57.

As shown in FIG. 3, the upper internal top area of the cap 52 also has a recessed heater assembly receiving area 53 adjacent the wick 60. The wick 60 is a firm rigid dimensionally stable member which is rectangular in cross-section and has flat faces. The wick face 61 has step configurations 62 and 64 which define the central wick section. The wick passes through the rectangular cap opening 54. The wick reduced central section between steps 62 and 64 engages the cap in a tight-fitting frictional engagement to provide an accurately positioned fit. The upper section of the wick which extends above the cap cavity section 53 is indented at 64, and provides a flat side moisture supplying surface 68 adjacent the top edge 66 and step of the wick 60.

Electrical energy is supplied to the vapor heating assembly through the pair of stainless steel support wire conductors, 58 and 59 which are embedded in the cap 52 (FIG. 3). Their upper sections 58a and 59a project upwardly vertically and extend above the cap on each side of the heating element holder casing 70 assembly. The two spaced electrical conductors, 58a and 59, one of which is shown at 58 (FIG. 3) have lower electrical section contact elements 58b (FIG. 3) and 59b (FIG. 2), which engage conducting elements of a switch assembly 120 (described below). The upper conductor sections 58a and 59a, conduct electrical energy to casing 70 of the vapor sealed heating assembly (FIG. 3), and also act as support members for it. The rigid support stainless steel wire upper ends 58a and 59a extend beside and project above the case 72, which is mounted on them. Note FIGS. 3 and 5. The stainless steel wires are both strong and corrosion resistant.

The wick material is a shaped and rigid light-weight, insulation material which is dimensionally stable and has a porous, non-woven fiber structure, reinforced in three dimensions to give it a rigid structurally stable shape characteristic. It is high-temperature resistant and can be cut to the desired shape. The undercut flat and firm upper face 68 is in very close proximity to the flat heating face of the heating assembly, with which it forms a narrow and thin vertical liquid vapor boiling chamber. The thinness of the boiling chamber, about 0.010 inches, gives a very efficient long thin chamber where a relatively large stream of vapor flows upwardly between the parallel metallic heating plate and the opposed liquid/moisture supplying wick face. The boiling chamber is most effective when the orientation of the chamber is vertical, encouraging vapor flow outwardly from the top of the chamber which is open. (See dashed vapor flow line S in FIG. 4).

The material PYROPEL™ MD-18 made by Albany International, Mansfield, Mass., is preferably used for the wick material. It has a nominal density of 18 pounds per cubic foot, and has good thermal resistance, withstanding temperatures of up to 550° F. The material is not affected by solvents, acids, and many alkali materials. The material also has good wicking and capillary action, which provides relatively high liquid carrying capacity. It can readily be cut and shaped and importantly will hold its shape and dimension. This is essential for its use as a working side of the steam vapor boiling chamber. The liquid conveyed by the wick is sufficient to provide required moisture for generating required vapor; about one fifteenth ounce per minute and yet limit excess moisture and liquid flow when the liquid container is not upright. The required level of liquid flow is provided regardless of the liquid container orientation.

The portion of wick 60 extending upwardly above the floor of cavity 53 is supported by a pair of upwardly extending plastic fingers molded with the cap 69. Each support finger is disposed along the rear side edge of the upwardly extending wick section in firm engagement to support the upper extending wick section in firm engagement with side 55 of heater assembly metal casing 70. The wick extends down to the bottom of bottle 80.

Figure 6:
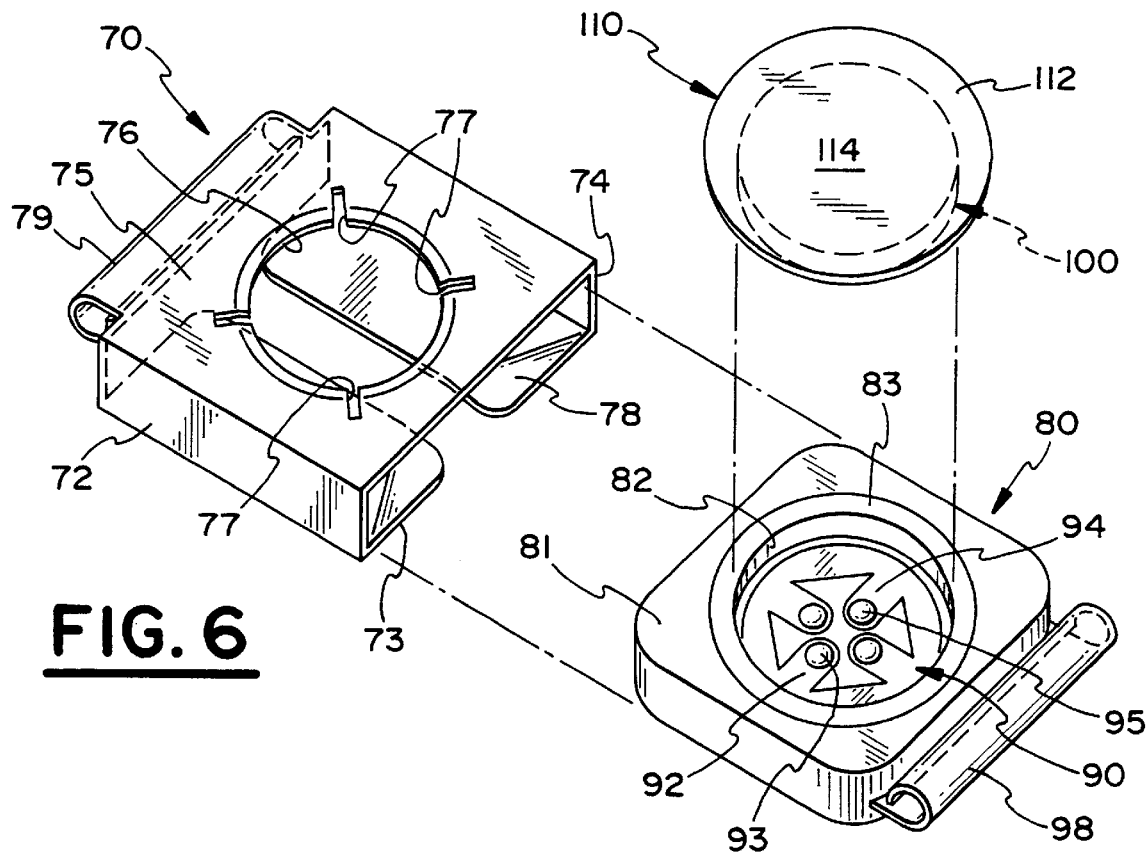
FIG. 6 is an exploded perspective view of the heating assembly showing the mounting and sealing components for the heating element.
Figure 7:
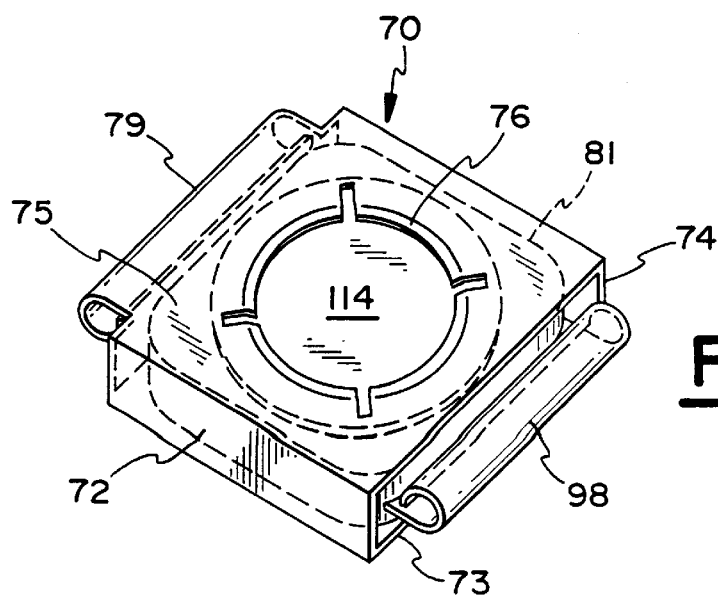
FIG. 7 is a perspective view of the assembled components of the heating assembly of FIG. 6.

Casing 70 (FIG. 6) of the heating assembly is an open sleeve rectangular piece. The sides 72, and 74 adjoin the wick contacting face 75. The boiling chamber face 114 for producing steam and vapor is within the circular opening defined by the annular bevel 76 and radial notches 77 (FIG. 7). The lower flanges 73 and 78 of casing 70 (FIG. 6) are spaced from each other to provide a longitudinally extending receiving slot.

An elongated cylindrical shaped electric wire and support engaging element 79 (FIGS. 5–7) is integrally connected to the side of face 75. It fits over the upper conducting wire support section 58*a*, and provides both support for the outer holder housing 70, and electrical connection to the face of PTC heating element 100 (FIG. 5). The tip of 58*a* is shown in FIG. 3. As seen in FIG. 3, the metal holder casing 70 fits down over the upper conducting wire section 58*a*. The lower side 74 of housing is brought to rest against the indented set back step 64 of which 60. The surface of the indented section 53 of cap 52 is below and spaced from the lower surface of case side 74 to achieve a higher heat transfer efficiency to the wick/water without losing energy by heating the cap. In this manner the upper portion of the wick and the casing surface 75 are immediately brought into firm, accurately positioned contact with each other. Enlarged sectional views of FIGS. 4 and 5 illustrate this firm engagement and positioning. This is an important requirement for an accurate dimension width of the boiling chamber in the gap formed between the wick surface 68 and the heating surface 114. This is essential for successful vapor generating operation.

Heat is produced by an electrically activated PTC (positive temperature coefficient) disk 100 which is encased in the molded plastic container case 80. The case construction is shown in FIGS. 6 and 8. Case 80 is an accurately molded plastic member having rigidity and resistance to high temperatures. It has a circular closure cap 86 mounted on a flexible support strap 85. The main body of the case is substantially rectangular and has a height which will permit it to be inserted within the metal holder 70, as illustrated in FIGS. 6 and 7. The PTC container case 80 is molded around the negative conducting plate 90 during the course of its manufacture, which assures very accurate positioning of the parts. Dimension tolerances are held to within two thousandths of an inch.

As illustrated in FIG. 8, the PTC container case internal annular wall 83 defines a cavity in which the PTC heating element disc 100 is received. An integral annular sealing ring 82 is disposed adjacent the annular wall 83. The other lower portion of the container case 80, on the other side of the conducting plate 90, has a circular internal cavity, defined by the circular wall 84 for receiving the circular closure cap 86. Closure cap 86 is flexibly joined to the main body of the container 80 by the flexible strap member 85, which forms a loop 87 (FIG. 5) when the closure cap 86 is inserted into the opening, as defined by circular wall 84. It closes and seals the opening to prevent moisture from entering the cavity and corroding the plate 90 and the PTC heating element. The strap 85 holds the disc in position, and is of a width that permits it to slide through the longitudinal receiving slot formed between the lower surface of holder casing 70 between its lower sides 73 and 78.

As shown in FIG. 8, the edges of the flat plate electrode 90 are embedded in the casing during molding such that the internal case portion 88 flows about the edge 91 of the flat plate-type electrode 90 to hold it accurately in position. In this way, the container case 80 provides a dimensionally accurate fit for firm engagement between the conducting plate 90 and the PTC heating element 100.

The flat plate electrode 90 is a resilient spring metal member of rectangular configuration having four radially extending electrical conducting fingers, such as finger 92, which have a contact button 93 on the free end thereof. The four fingers extend radially inwardly toward each other. Each of them is spaced from and opposed as shown by opposed finger 94 and its contact button 95. The upper surface of all four contact buttons are in the same plane and have an upper contact surface 96 (FIG. 8) which engages the innermost surface of the PTC heating element 100.

The open hollow cylindrical support element 98 along the side of the flat electrode 90 fits over and slides down on the second upstanding upper section 58*b* of electrical wire support conductor 58. The sectional view of FIG. 5 illustrates the fit of the holder casing 70 and its electrode plate 90 on the upper sections 58*a* and 58*b* of conductor wires 58 and 59 to hold case 70 in rigid, accurate position.

The container 80 is molded semi-hard silicone because it must have approximate sealing of PTC heating element 100 against annular sealing ring 82 and within the annular wall 83 of container 80. It is a precision molded piece with dimensional tolerance of two thousandths of an inch. The diameter of the upper annular cavity wall is 0.46 inches and the depth from the top surface of the seal ring 83 to the top surface 96 of contact buttons 93 of the four spring-like conducting arms is 0.044 inches.

The heating assembly of the PTC heating element and plate 110 fit into the upper cavity of container case 80, defined by cavity wall 83. The PTC heating element 100 is electrically and thermally bonded to the circular heating plate, with a uniform layer of silver epoxy TRA-duct HP 2958 or P/N907-104 along the interface of the two pieces to assure the most efficient heat transfer. The circular plate 110 is nickel-silver metal having a satin finish. It is a hydrophilic material and provides a smooth boiling cavity heating surface 114 (FIG. 5). The outer peripheral edge section 103 of the heater plate 110 can be straight or angled downward as shown at 112 in FIG. 5, to overlay the annular seal 83 on container 80.

Assembling of the heater assembly simply involves closing of the container 80 by placing closure cap 86 in the lower cavity, then inserting the PTC heater element 100, and heater element plate 110, into fitting engagement with the upper cavity. The assembled units are then slipped into the metal holder casing 70 to provide the completed heating assembly shown in FIG. 7. The assembly is then mounted on the upper sections 58a and 59a of wire conductors 58 and 59. This assembly provides a vapor sealed arrangement for the PTC heating element 100 where the interface between the conducting electrode plate 90 and the PTC element 100 is completely sealed to preclude galvanic exposure to moisture and possible galvanic corrosion. The casing 70 for the heater assembly provides the other electric connection for the PTC element, when it comes into contact with the conductive heater plate 110, which is in direct contact with the PTC heater element 100.

It is important to note, as illustrated in the cross-sectional view of FIG. 5, that the outer surface 75 of casing 70 and the inwardly turned circular seal edge 76, provide an accurate spacer between the inner face 68 of wick 60, and the circular exposed portion of outer face 114 of the heater plate 110. These two opposed surfaces form a boiling chamber 118 between them, where the moisture supplied by the wick face 68, and the heat from plate surface 114 meet to produce steam and vapor.

The upper ends 58a and 59b of the conductors, which are sufficiently strong stainless steel wire, extend up from molded cap 52 to provide firm, accurate support members for the heater assembly, when support cylinders 79 and 98 are mounted on them.

This support arrangement of the heater assembly provides the capability for an accurate fit of parts to maintain the close spacing tolerance required between the dimensionally stable and flat inner wick surface 68 and the heater plate 114. The distance between the two surfaces is preferably maintained at about 0.010–0.040 inches. This arrangement eliminates the problem of manually attempting alignment of such an accurate spacing between the two interactive surfaces of the boiling chamber. This is accomplished by providing a common and accurate mounting base in the cap 52 (FIG. 3) for both the moisture conveying wick 60 and the heater assembly case 70 for the PTC heater element.

It should be noted that encasing the PTC heating element in a sealed vapor-free container 80 provides a dimensionally accurate and reliable electrical contact assembly, and also one that is not subject to galvanic corrosion. The accurate and rapid assembly of the involved elements is assured by mounting the wick and heating assembly in their respective places on the cap with a fast assembly procedure that does not require accurate final adjustment and highly skilled labor. The outer metal case 70 is made of electroless nickel plated phosphor bronze stock of 0.010 inches with the inturned circular edge 76 displacing an additional 0.005 inches. This outer sleeve-like holder case 70 acts as an electrical conducting electrode for the heater assembly.

The PTC element 100 is a commercially available positive temperature coefficient disc sold by Siemens Components, Inc. of Iseline, N.J., part no. B59060-A220-A10. It operates at a temperature of approximately 100 degrees centigrade in the unit. During water boiling/vaproization and can reach 200° C. after the water in the wick is evaporated completely. This operation temperature of 100° C. is quickly reached to heat the space of the boiling chamber 118.

The cross-sectional views shown in FIGS. 4 and 5 illustrates the gap between heater plate surface 114 and the inner face 68 of wick 60. This gap is approximately 0.010 inches, but it can vary depending on the wick material. Because of the close spacing and fast heating of the PTC element 100, steam is generated very quickly. Quick heating is important for a consumer unit. It should also be noted that the top surface 66 of the wick is substantially below the uppermost portion of the circular inturned edge 76 of plate 75. This permits the instant escape of the steam vapor. Approximately one eighth ounce of liquid is vaporized by the assembly in two minutes. The bottle 80 holds one ounce. All metal surfaces of the boiling chamber and the wick are hydrophilic.

As shown in FIG. 2, the device is powered by a low voltage supply via an commercially available 120 volt electrical AC/AC converter wall plug unit and a wire with a jack. The jack is connected to the device electrical switch assembly 120. An on-off slide switch 122 is mounted to the circuit board 124. The conducting jack is inserted at the lower end of the housing 10 at 17 and through the opening 125, and into the electrical jack receptacle 128 connected to switch 122. Two parallel wire conductors 126 (only one of which is shown in the drawings) engage the pair of wire conductors 58 and 59 rigidly fixed in the cap 52. As shown, conductor 126 engages 59b. As shown, spring-like wiper conductor 126 engages the conductor lower section 59b, while the conductor 128 similarly engages the conductor lower section 58b of the conductors.

Also as shown in FIG. 2, disposed between the two spaced lower conductor wire sections 58b and 59b projecting from the cap 52, is the cap support piece 130. Support piece 130 is integrally connected to the cap and has a lower flexible depending member 132 with an inwardly extending tooth 134. Housing 10 at the open bottom lower section at recess section 16 has an upwardly extending internal retaining wall 136. It has opening 137, into which the tooth 134 extends. In this manner the cap 52 for the bottle 80 is held rigidly, but removably in position within the housing. The bottle 80 itself is inserted and removed through the bottom end of the housing by merely grasping its lower end through recess 16 and unscrewing it from the cap 52. The bottle then is refilled and then reinserted in the housing.

FIG. 9 shows a brush assembly 140, which also can be mounted on the housing, instead of the open frame assembly 20 of FIG. 2. The cross-section view of FIG. 9 shows the construction of the brush assembly 140. It has an upper plate and brush support member 142 with vapor openings 143 through which water vapor passes. A lower depending flange 144 fits over the upper forward end of the housing in place of the open frame assembly 20 and engages the circular housing bearing member 26. Interior and circularly arranged fingers 146, 147 engage the central spindle support assembly 30. Retaining fingers 31 extend through and lock behind the opening 145. The plurality of groups of soft bristles 148 are mounted in receiving openings 149 to provide a composite flat circular brush surface 150.

OPERATION

The unit is placed in operation when the bottle 80 is filled with fluid and inserted into the housing where it engages and is retained by the threads of cap 55 of the cap 52. Plain ordinary water, or water mixed with water soluble skin treatment substances can be used. When heated such will provide a steam vapor.

The electrical jack is inserted in the open bottom of the housing and through the opening 125 to connect with the electrical switch assembly. The buffing pad 28, which has a generally pan shaped configuration, as shown in FIG. 2 (at slightly less than twice actual size of the units built and tested), is placed on the rotatable open support frame 22, where it is held in position against the ground by the ring-shaped hook-type retaining member 27.

The user then grasps the lower section of the housing 14 in the palm of the hand and activates on the sliding power switch 122. Electrical energy from the circuit board 124 is then applied to both the PTC heating assembly 70 through the conductors 58 and 59 and to the electric motor of 40. Two wires connected to the electric motor (a typical two wire circuit connection) are not shown.

The motor will immediately begin to revolve the open frame movable skin contacting assembly 20 as well as the vapor propelling fan blades 46. Air will be moved into the housing through opening 18 as indicated at A-1, and passed over and through opening 47 as indicated in A-2 to provide air flow over the wick 60 and PTC heating assembly 70. From there it is directed forwardly as indicated by the dotted line A-4 to the rotating frame 22. The fan blades will rotate at the rotational speed of the motor, while the rotating frame 22 and buff surface of pad 28 rotates at a much slower speed of only several hundred revolutions per minute. The air intake opening 18 provides the means to control the temperature of the vapor by adding a stream of cool air A-3.

The small one ounce fluid bottle 80 and short wick 60 (2 inches from tip to tip, although it extends to the bottom of the bottle), provide a unique fluid source which is continuous and non-spillable regardless of the housing orientation. The fine dense compressed fibers (0.001 in.) of the ¼×½ inch wick supply about one eighth ounce of liquid every two minutes. This relatively high flow rate for the size, and the use of the upper web surface for a boiling chamber face, contribute to the substantially high vapor production rate (for its size) of the small assembly.

The vapor sealed arrangement of the PTC heating element, and the accurate positioning of the heating assembly parts assure reliable and trouble-free long operating life of the device.

After the unit is turned on, the vapor generating assembly 60 and 70 will quickly heat (about 1 minute) and begin producing a stream of steam water vapor which enters the air stream A-2–A-4, and passes to the rotating buff pad 28, through which it passes. Note that the vapor generator is close (about 1 ½ inches) to the buff pad, so that the vapor path is short to minimize temperature drop, loss of vapor and decreased vapor flow.

The buff pad, which has a porous fiber construction, allows the vapor to pass through it, and in doing so, vapor condenses on the pad, which will then impart a warm, moist layer of vapor condensate to the skin surface.

The rotating pad is held against the surface to be treated, such as the cheek. It should be noted that the gear reduction assembly prevents motor stalling and undue loss of motor speed when the pad is applied to the skin surface.

The construction of the frame 22, with its side 24 flange, gives an ability to simultaneously reach adjoining skin surfaces that are recessed and angularly inclined to each other, such as the adjoining cheek and nose surface. The buff pad side surface 29 and periphery of the central portion of the flat main pad surface intersect to make a peaked and angular linear circular section 29a. This angular section permits treatment of recessed angular areas.

The rotating pad surface is held against the skin surface to be treated for 10–20 seconds, and then slowly moved to adjacent skin surfaces. It will gently provide a warm, moist layer of moisture, which opens skin pores and maximizes the effect of the buffing and cleansing action of the moving pad surface. The result is a very noticeable improvement in skin texture and a pleasant feeling of refreshment of the skin surface.

This device provides a user operated, safe method of using a water vapor and buffing treatment to the skin surface with a self-contained unit, which is convenient to use.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

What is claimed is the following:

1. A skin moisturizing and buffing device, comprising:
   a) a hand-held housing;
   b) an external support assembly rotatably mounted on the housing and having an external support member which is relatively movable with respect to the housing, and which has a relatively large and relatively flat support area having spaced support elements defining relatively large open spaces through which water vapor may pass;
   c) a removable thin, porous relatively large area skin buffing fibrous material having a relatively rough skin engaging surface, which is mounted on and supported by the support member and through which water vapor can pass and on which it can condense so as to moisten and buff the skin surface when placed in sliding contact therewith to thereby simultaneously give a gentle exfoliating action of the skin surface;
   d) a vapor generating assembly, within the housing adjacent and close to the movable support member, which generates water vapor for the skin buffing element;
   e) a mechanical power assembly within the housing and connected to the movable support assembly which provides mechanical movement to the support assembly; and
   f) a vapor propelling assembly disposed in the housing adjacent and close to the vapor generating assembly which moves vapor from the vapor generating assembly to the skin buffing element.

2. A skin moisturizing and buffing device as set forth in claim 1, wherein:
   a) the periphery of the movable support frame is substantially circular; and
   b) the support frame moves in a circular direction around a central axis.

3. The skin moisturizing and buffing device as set forth in claim 2, wherein:
   a) the support frame includes a fastening element; and
   b) the skin buffing element is engaged by the fastening element to hold it in position on the support frame.

4. The skin moisturizing and buffing device as set forth in claim 1, wherein:

a) the skin buffing element has a pan-shaped configuration; and b) the movable support frame has a configuration which will receive and uniformly support the entire skin buffing element.

5. The skin moisturizing and buffing device as set forth in claim 1, wherein:

a) the mechanical power assembly includes a small electrically powered motor which provides the mechanical power for the assembly; and b) at least one speed reduction gear stage is mechanically connected between an output shaft of the motor and the movable support assembly, for reducing the output speed delivered by the assembly, and to also provide mechanical resistance to either the stalling of the motor or undue loss speed of the frame when the skin buffing element is applied to the skin.

6. The skin moisturizing and buffing device as set forth in claim 1, wherein:

a) the vapor generating assembly includes a liquid conveying element and an electrical heating assembly disposed immediately adjacent and in very close proximity to each other so as to form a boiling chamber for producing vapor.

7. The skin moisturizing and buffing device as set forth in claim 6, wherein:

a) the liquid conveying element is a heat resistant fibrous wick with a moisture providing surface; and b) the heating assembly has a heat transmitting surface which is directly opposed to the moisture providing surface and is in very close proximity thereto.

8. The skin moisturizing and buffing device, as set forth in claim 1, wherein:

a) the housing contains a removable liquid container for holding a water-based liquid to be supplied to the vapor generating assembly.

9. The skin moisturizing and buffing device as set forth in claim 1, wherein:

a) a hand-held housing;

b) a movable support assembly mounted on the housing having an external movable support frame relatively movable with respect to the housing, which has a relatively large and relatively flat support area through which water vapor may pass;

c) a relatively large area skin buffing element having a skin engaging surface, which is mounted on and supported by the frame and through which water vapor can pass and on which it can condense;

d) a vapor generating assembly, within the housing adjacent and close to the movable support frame, which generates water vapor for the skin buffing element;

e) a mechanical power assembly within the housing and connected to the movable support assembly which provides mechanical movement to the support assembly; and f) a vapor propelling assembly disposed in the housing adjacent and close to the vapor generating assembly which moves vapor from the vapor generating assembly to the skin buffing element;

g) the vapor generating assembly includes a liquid conveying surface and an electrical heating assembly are disposed immediately adjacent and in very close proximity to each other so as to form a boiling chamber for producing vapor h) the boiling chamber for producing vapor is formed between the metal heating surface of a PTC heater assembly and the adjacent liquid conveying surface positioned parallel to said metal heating surface; and i) the boiling chamber is vertically oriented, whereby the top section of said boiling chamber is open to facilitate instant escape of the water vapor or steam, thus avoiding re-condensation of the steam in the liquid conveying element.

10. A skin moisturizing and buffing device, comprising:

a) a hand-held housing;

b) a movable support assembly mounted on the housing having an external movable support frame relatively movable with respect to the housing, which has a relatively large and relatively flat support area through which water vapor may pass;

c) a relatively large area skin buffing element having a skin engaging surface, which is mounted on and supported by the frame and through which water vapor can pass and on which it can condense;

d) a vapor generating assembly, within the housing adjacent and close to the movable support frame, which generates water vapor for the skin buffing element;

e) a mechanical power assembly within the housing and connected to the movable support assembly which provides mechanical movement to the support assembly; and f) a vapor propelling assembly disposed in the housing adjacent and close to the vapor generating assembly which moves vapor from the vapor generating assembly to the skin buffing element;

g) the vapor generating assembly includes a liquid conveying element and an electrical heating assembly disposed immediately adjacent and in very close proximity to each other so as to form a boiling chamber for producing vapor;

h) the liquid conveying element is a heat resistant fibrous wick with a moisture providing surface; and i) the heating assembly has a heat transmitting surface which is directly opposed to the moisture providing surface and is in very close proximity thereto.

11. The skin moisturizing and buffing device as set forth in claim 10, wherein:

a) the wick surface and the heat transmitting surface are flat surfaces extending parallel to each other and are hydrophilic; and b) the source of the heat for the heating assembly is a PTC heating element.

12. The skin moisturizing and buffing device as set forth in claim 10, wherein:

a) the vapor generating assembly includes a common support member within the housing having a support element for both the wick, and for the heating assembly; and b) the support member includes elements which permit precision assembling of the wick and the heating assembly with respect to each other and the support to form the boiling chamber.

13. The skin moisturizing and buffing device, as set forth in claim 10, wherein:

a) the heating assembly has a PTC heating element electrically and thermally bonded directly to the heat transmitting surface; and b) the PTC heating element is completely sealed to preclude exposure to moisture.

14. A skin moisturizing and buffing device, comprising:

a) a hand-held housing;

b) an external skin contacting assembly rotatably mounted thereon which has a relatively large and relatively flat external support member having spaced support elements defining relatively large open spaces through which water vapor can readily pass, and on which a thin, porous relatively, rough, fibrous skin contacting material is removably mounted, the support member having spaced support elements defining relatively large open spaces for allowing water vapor to pass therethrough and condense on the material to moisten and buff the skin surface when the skin contacting material is placed in sliding contact therewith, simultaneously providing a gentle exfoliating action of the skin surface;

c) a mechanical power assembly disposed within the housing and connected to the external skin contacting assembly for moving it relative to the housing so as to provide a light sliding contact with the skin;

d) a small refillable liquid container mounted within the housing which will hold a water-type liquid to be vaporized and subsequently applied to the skin by the skin contacting surface;

e) a liquid conveying assembly within the housing and connected to the liquid container, which conveys liquid from the liquid container;

f) a compact vapor producing assembly within the housing and disposed adjacent to the liquid conveying assembly which receives the liquid supplied from the container and converts it to steam and water vapor to be supplied to the skin contacting assembly; and g) a vapor propelling assembly disposed in the housing adjacent and close to the vapor producing assembly which moves vapor from the generating assembly to the support member and skin contacting material.

15. The skin moisturizing and buffing device as set forth in claim 14, wherein:

a) the skin contacting surface includes a skin buffing element, which is a pliable, thin, porous layer for contacting a skin surface is mounted on the movable, relatively large area movable skin contacting assembly.

16. The skin moisturizing and buffing device as set forth in claim 14, wherein:

a) the liquid conveying assembly is a heat resistant fibrous wick mounted on and extending into the liquid container; and b) the wick has an external section extending above the container and close to and immediately adjacent to the vapor generating assembly.

17. The skin moisturizing and buffing device as set forth in claim 14, wherein:

a) the vapor producing assembly has a heat producing surface which is directly opposed to a flat surface of the wick and is in very close proximity thereto to form a boiling chamber.

18. The skin moisturizing and buffing device as set forth in claim 17, wherein:

a) the vapor producing assembly includes a heating assembly which has a positive temperature coefficient element.

19. The skin moisturizing and buffing device as set forth in claim 14, wherein:

a) a vapor propelling assembly is disposed within the housing adjacent to the vapor producing assembly and has a fan, mechanically connected to the mechanical power assembly, which propels a steady flow of the vapor to the skin contacting surface.

20. The skin moisturizing and buffing device as set forth in claim 14, wherein:

a) the liquid conveying assembly is a heat resistant fiber wick which is dimensionally stable; and b) the liquid vapor producing assembly includes a PTC heating element which is immediately adjacent to the wick for generating water vapor.

21. The skin moisturizing and buffing device as set forth in claim 20, wherein:

a) The skin contacting surface is a fibrous skin buffing element, which provides the thin, porous surface for contacting a skin surface and which is removably mounted on the movable, relatively large area movable skin contacting assembly.

22. The skin moisturizing and buffing device as set forth in claim 14, wherein:

a) the support member and the overlying skin contacting material is configured to simultaneously engage the apex area formed by two inclined converging skin surfaces.

23. The skin moisturizing and buffing device as set forth in claim 14, wherein:

a) the support member has a fastening element thereon;

b) the skin contacting material overlies the support member and is held in position thereon by the fastening element of the support member.

24. The skin moisturizing and buffing device as set forth in claim 14, wherein:

a) the liquid vapor producing assembly includes a support element for the liquid vapor producing assembly and which also provides common support for the liquid conveying assembly to permit accurate assembly and relative alignment of the assemblies.

25. A skin moisturizing and buffing device, comprising:

a) a housing;

b) an external support assembly rotatably mounted on the housing and having an external movable open relatively large and relatively flat support member with spaced support elements defining open spaces, and, an overlying fibrous thin, porous, relatively rough skin engaging buffing material, covering the support member, through which water vapor may pass and condense such that sliding contact with the skin surface provides a light exfoliating effect on the skin;

c) a vapor generating assembly within the housing including:

1. a container for holding a water type liquid;
2. a wick disposed in the container and extending outward therefrom for moving the liquid in the container to an external section of the wick;
3. a heating assembly disposed in said housing;
4. said heater assembly including a heat producing surface which is both closely spaced and opposed to a surface on the external section of the wick, thereby defining a chamber within which water vapor is generated; and
5. said heater assembly including a positive temperature coefficient element as the heat source;

d) a mechanical power assembly within the housing and connected to the movable support assembly which provides mechanical movement to the support assembly; and, e) a vapor propelling assembly disposed in the housing adjacent and close to the vapor generating assembly which moves vapor from the vapor generating assembly to the skin buffing element.

26. The skin moisturizing and buffing device as set forth in claim 25, wherein:
 a) the heat producing surface of the PTC element assembly is hydrophilic.

27. The skin moisturizing and buffing device as set forth in claim 26, wherein:
 a) the wick and the heating assembly are mounted on a common support member having structure for precisely receiving and supporting the assemblies with respect to each other.

28. The skin moisturizing and buffing device as set forth in claim 25, wherein:
 a) the support member has a retaining element thereon for fastening the skin engaging material, to permit the material to be firmly held in position on the frame and also to be readily removed after use.

29. A skin moisturizing and buffing device, comprising:
 a) a hand-held housing;
 b) an external support assembly rotatable mounted on the housing and having an external support frame which is relatively movable with respect to the housing, and which has a relatively large and relatively flat support area having spaced support elements defining relatively large open spaces through which water vapor may pass;
 c) a removable thin, porous relatively large area skin buffing fibrous material having a relatively rough skin engaging surface, which is mounted on and supported by the frame and through which water vapor can pass and on which it can condense so as to moisten and buff the skin surface when placed in sliding contact therewith to thereby simultaneously give a gentle exfoliating action of the skin surface;
 d) a vapor generating assembly, within the housing adjacent and close to the movable support frame, which generates water vapor for the skin buffing element;
 e) a mechanical power assembly within the housing and connected to the movable support assembly which provides mechanical movement to the support assembly; and
 f) a vapor propelling assembly disposed in the housing adjacent and close to the vapor generating assembly which moves vapor from the vapor generating assembly to the skin buffing element;
 g) the vapor generating assembly includes a liquid conveying element and an electrical heating assembly disposed immediately adjacent and in very close proximity to each other so as to form a boiling chamber for producing vapor
 h) the boiling chamber for producing vapor is formed between the metal heating surface of the PTC heater assembly and the adjacent liquid surface positioned parallel to said metal heating surface; and
 i) the boiling chamber is vertically oriented, whereby the top section of said boiling chamber is open to facilitate instant escape of the water vapor or steam, thus avoiding re-condensation of the steam in the liquid conveying element.

* * * * *